(12) United States Patent
Mühlbauer

(10) Patent No.: US 10,603,184 B2
(45) Date of Patent: Mar. 31, 2020

(54) INTERVERTEBRAL DISC IMPLANT AND METHOD FOR RESTORING FUNCTION TO A DAMAGED FUNCTIONAL SPINAL UNIT

(71) Applicant: Manfred Mühlbauer, Giesshübl (AT)

(72) Inventor: Manfred Mühlbauer, Giesshübl (AT)

( * ) Notice: Subject to any disclaimer, the term of this patent is extended or adjusted under 35 U.S.C. 154(b) by 337 days.

(21) Appl. No.: 15/326,976

(22) PCT Filed: Jul. 17, 2015

(86) PCT No.: PCT/EP2015/066401
§ 371 (c)(1),
(2) Date: Jan. 17, 2017

(87) PCT Pub. No.: WO2016/012361
PCT Pub. Date: Jan. 28, 2016

(65) Prior Publication Data
US 2017/0202676 A1    Jul. 20, 2017

Related U.S. Application Data

(60) Provisional application No. 61/999,184, filed on Jul. 19, 2014.

(51) Int. Cl.
*A61F 2/44* (2006.01)
*A61F 2/30* (2006.01)

(52) U.S. Cl.
CPC .............. *A61F 2/4425* (2013.01); *A61F 2/44* (2013.01); *A61F 2002/30158* (2013.01); *A61F 2002/30301* (2013.01); *A61F 2002/30518* (2013.01); *A61F 2002/30649* (2013.01); *A61F 2002/30841* (2013.01); *A61F 2002/30904* (2013.01); *A61F 2002/443* (2013.01)

(58) Field of Classification Search
CPC ............................... A61F 2/442; A61F 2/4425
See application file for complete search history.

(56) References Cited

U.S. PATENT DOCUMENTS

| | | | |
|---|---|---|---|
| 6,994,727 B2 * | 2/2006 | Khandkar | A61F 2/4425 606/247 |
| 2013/0110240 A1 * | 5/2013 | Hansell | A61F 2/4425 623/17.16 |

* cited by examiner

*Primary Examiner* — Si Ming Ku
(74) *Attorney, Agent, or Firm* — Nixon & Vanderhye P.C.

(57) ABSTRACT

Presented are intervertebral disc implants (20) for the total replacement of an intervertebral disc (3) within the cervical spine, comprising two articulating members (21, 25), where the inferior member (21) on its upper surface is adapted for engaging an upper vertebral body (1) and its lower surface has an convex projection (23), and the inferior member (25) on its lower surface is adapted for engaging a lower vertebral body (4) and its upper surface has an saddle shaped projection (27), which is convex in its longitudinal anterior-posterior profile and which is concave in its transversal lateral profile with the general same diameter as the convex projection (23) of the superior member (21), therefore allowing flexion-extension-motion over a variable center of rotation, and in addition allowing rotation and lateral bending through a second independent center of rotation which is located above the intervertebral disc implant (20) at a distance which is defined by the diameter of the convex projection (23) of the superior member (21), therefore allowing coupled motion for rotation and lateral bending independently from flexion/extension, and therefore more closely replicating the natural kinematics of a cervical disc.

11 Claims, 14 Drawing Sheets

INTERVERTEBRAL DISC IMPLANT AND METHOD FOR RESTORING FUNCTION TO A DAMAGED FUNCTIONAL SPINAL UNIT

CROSS REFERENCE TO PRIOR APPLICATIONS

Priority is claimed U.S. Provisional Application 61/999,184 filed Jul. 19, 2014 and to PCT/EP/2015/066401 filed Jul. 17, 2015.

FIELD OF THE INVENTION

The invention relates to an intervertebral disc implant for the total replacement of an intervertebral disc of the cervical spine and to a method for restoring function to a damaged functional spinal unit using such an intervertebral disc implant.

BACKGROUND OF THE INVENTION

Cervical disc prostheses have been in clinical use for total disc replacement in the cervical spine for more than 10 years. Motion preservation or restoration after cervical discectomy by the use of a disc prosthesis is believed to be advantageous compared to fusion with respect to certain biomechanical considerations. Fusion of a cervical spinal motion segments leads to significant increase of intradiscal pressure at the adjacent segments. Therefore, fusion might be a trigger for accelerated adjacent segment degeneration. Fusion after cervical discectomy also decreases or at least changes the range of motion of the cervical spine to a greater extent than arthroplasty. Typically, patients are found to be back to their daily activities quicker after arthroplasty than after fusion.

It is generally accepted that a cervical disc prosthesis should replicate the kinematics of a natural cervical disc as closely as possible. The disc prosthesis should be able to follow the natural motion of the respective motion segment after its implantation. If the biomechanical design of a disc prosthesis is inadequate, then the motion segment may not move naturally but is forced to follow the biomechanics of the prosthesis. Such unnatural motion may cause increased stress to the facet joints and painful facet degeneration, further it may cause increased stress forces at the contact area of the prosthesis with the adjacent vertebral bodies endplates thus leading to implant migration into the vertebral bodies or even implant displacement. Further, it must be presumed that biomechanically inadequate disc prostheses also change the kinematics at the adjacent motion segments and therefore bear a similar risk for adjacent segment degeneration than conventional fusion.

Accordingly, before designing a cervical disc prosthesis, the kinematics of a natural cervical motion segment must be fully understood. Several independent motion properties are found in a cervical motion segment. There is flexion-extension motion which is coupled to mild anterior-posterior translation. Translation is mainly found in the cranial segments and gradually decreases from C3/4 to C6/7 (the C 2/3-motion-segment is mostly excluded in the respective studies in the literature, most probably because the indications for total cervical arthroplasty generally include the segments from C3/4 to C6/7). This motion pattern is determined by a center of rotation (COR) which is found approximately at the level of the upper endplate of the C7-vertebra at C6/7 and which gradually moves caudally for the cranial motion segments being approximately 12 mm below the upper C4-endplate for the C3/4-segment. In addition, there is coupled motion for side-bending and rotation between C3 and C7: every side-bending at these cervical motion segments also leads to ipsilateral rotation, and rotation leads to ipsilateral side-bending. This motion pattern is defined by a center of rotation or "COR" which is entirely independent from the previously described COR for flexion-extension and is found superior to the lower endplate of the upper vertebra of the respective motion segment. This coupled side-bending/rotation is facilitated around a longitudinal anterior-posterior axis through the respective COR following an oblique direction approximately crossing the anterior edge of the lower endplate of the upper vertebra and finally crossing the posterior edge of the upper endplate of the same vertebra.

In order to allow natural motion a cervical disc prosthesis must closely replicate the above mentioned biomechanical properties and must definitely allow motion through two independent CORs.

Moreover, the prosthesis COR for flexion-extension must be variable in order to replicate the different kinematics for the upper and the lower cervical spine. Finally, inter-individual differences for the respective patient's COR should be taken in account, and also the fact that candidates for cervical disc surgery often present degenerative changes at the entire cervical spine also affecting kinematics of their motion segments.

In order to achieve motion through two independent CORs, a three piece prosthesis with two endplates and an inlay offers greater flexibility with respect to its biomechanical design than a two piece construct. Such a three piece prosthesis with two independent gliding pairs—upper prosthesis-endplate versus upper surface of inlay, and lower surface of inlay versus lower prosthesis endplate potentially bears the property of including two independent motion patterns in a single prosthesis. Nevertheless, hardly any of the presently available three piece prosthesis fulfill the above mentioned biomechanical requirements. With exception of the Bryan-prosthesis, which closely replicates natural motion, most other three piece prostheses lack adequate biomechanical properties. None of the three pieces prostheses types disclosed in patent US 2010/0137992 A1 demonstrates a COR for side-bending/rotation above the implant as described above, neither a sufficiently variable COR for flexion/extension as described above. The two piece prosthesis which is disclosed in patent US 2010/0137992 A1 shows different diameters for flexion/extension and side-bending/rotation, however the COR for side-bending is below the implant and therefore may not provide natural motion. The drawings of patent US 2005/0228497 A1 show a disc prosthesis with several embodiments: some of the figures demonstrate unphysiological posterior translation in flexion and anterior translation in extension; other figures disclose saddle-like articulating surfaces allowing near—physiological translation with flexion/extension, but according to these drawings any rotation would cause craniocaudal distraction of the implant which is entirely unphysiologic.

A brief overview of spinal anatomy and terminology will be beneficial in explaining one or more aspects of the inventions described herein. FIG. 1A shows a functional spinal unit from a lateral or sagittal view having a bony superior or upper vertebral body 1 having a vertebral endplate 2 connected to a bony inferior or lower vertebral body 4 via an intervertebral disc 3 comprised of an outer ring of fibrous collagen material (the annulus) surrounding an inner amorphous mass of material, the nucleus pulposus. Also shown are the posterior elements including the spinous process 5, pedicle 6, facet joint 7 and transverse process 8. FIG. 1B shows a vertebral body 1, 4 from a transverse plane view or an axial cross-section along the cranial caudal axis. The front or anterior portion of the vertebral body 1, 4 is curved and the posterior portion is relatively flat. Further posterior lie the facet joints 7 and other posterior elements and various ligaments (not shown).

SUMMARY OF THE INVENTION

One or more embodiments of the invention disclosed herein provide improved two part intervertebral or cervical disc implants for total cervical disc replacement which have two separate independent CORs for flexion/extension and side-bending/rotation and the COR for flexion/extension is operable to be widely variable and further, the range of motion for side-bending and coupled rotation is hardly restricted by the flexion/extension angle after implantation. The implant or prosthetic designs disclose a convex curvature at the upper prosthesis-endplate which is congruent to a both concave-convex saddle-like gliding surface at the lower prosthesis-endplate therefore facilitating anterior posterior translation and distribution of compressive forces over a greater contact area and avoiding point-like contact of the two articulating surfaces. The edge-design of one or more of the disclosed prostheses allow unrestricted motion for flexion/extension, side-bending and rotation within the physiological range of motion of a cervical motion segment, independent from the angle of prosthesis-implantation and independent from the momentary position of its endplates, therefore avoiding the risk of implant-loosening caused by high shear forces created from edge-contact, and therefore replicating natural conditions, where motion is mainly controlled and restricted by the uncovertebral joints, the facet joints and the posterior longitudinal ligament. Thus, the outer edges or the periphery of the members do not interfere with the motion of the implant or contact each other when positioned between opposing vertebral bodies.

In one embodiment provided herein an intervertebral disc implant may include a first or superior member including a first articulating surface formed in the shape of a convex projection and a second opposing surface configured to engage a first vertebral endplate and a second or inferior member including a second articulating surface, this surface further defines an extension having a saddle shaped projection with convex profile along a first axis and concave profile along a second axis perpendicular to said first axis and a second opposing surface configured to contact a second opposing vertebral endplate. In use, the first articulating surface rides along the convex portion of the second articulating surface in an arcuate path along the first axis thereby allowing multiple centers of rotation between said members and allowing travel along the first axis.

Each member may include a baseplate and/or and anchor from which the bearing surface extends.

The convex projection on the first articulating surface can optionally be convex along more than one axis, in three dimensions and/or asymmetrical about two or more axes.

In some embodiments one or more kinematic conditions may apply: the rotation between the convex projection and the saddle shaped projection is not limited; translation between the convex projection and the saddle shaped projection along the first axis is curvilinear; translation between the convex projection and the saddle shaped projection along the second axis is limited; translation between the convex projection and the saddle shaped projection along the second axis is prevented; translation along the medial lateral axis is limited; wherein translation along the medial lateral axis is prevented.

Also presented is method of restoring function to a damaged functional spinal unit using such an intervertebral disc implant which involves:

establishing along a first endplate of an upper vertebral body a first articulating surface formed in the shape of a convex projection, said first articulating surface having a second opposing surface configured to contact a first vertebral endplate;

establishing along a second endplate of an opposing lower vertebral body a second articulating surface having a saddle shaped projection with convex profile defining an anterior-posterior axis (first axis) and concave profile defining a medial-lateral axis (second axis), said second articulating surface having a second opposing surface configured to contact a second opposing vertebral endplate of the lower vertebral body;

mating said two articulating surfaces such that the first articulating surface rides along the convex portion of the second articulating surface in an arcuate path along the anterior-posterior axis thereby allowing multiple centers of rotation between said members and limiting translation along said anterior-posterior axis.

Another method described herein for restoring function to a damaged functional spinal unit using such an intervertebral disc implant including two opposing vertebral body endplates involves the following steps:

implanting along a first endplate of an upper vertebral body a first or superior member including a first articulating surface, said surface defining an extension with a convex profile and wherein said articulating surface has second opposing surface, opposite said articulating surface, configured to engage a first vertebral endplate of the upper vertebral body;

implanting along a second endplate of a lower vertebral body a second or inferior member including a second articulating surface, said surface defining an extension having a saddle shaped projection with convex profile along a first axis and concave profile along a second axis perpendicular to said first axis and a second opposing surface, opposite said articulating surface, configured to contact a second opposing vertebral endplate of the lower vertebral body;

engaging said articulating surfaces such that the first articulating surface is operable to translate along the convex portion of the second articulating surface in an arcuate path along the first axis thereby allowing multiple centers of rotation between said members and allowing travel along the first axis.

Finally, these methods may further includes a step wherein inserting the second articulating along a surgical approach that is not collinear to a patient's anterior posterior axis and then mating said surface it with the first articulating surface and thereafter rotating said second surface such that said convex profile second surface is collinear with the anterior-posterior axis of the second endplate.

DETAILED DESCRIPTION

Figure 1A:
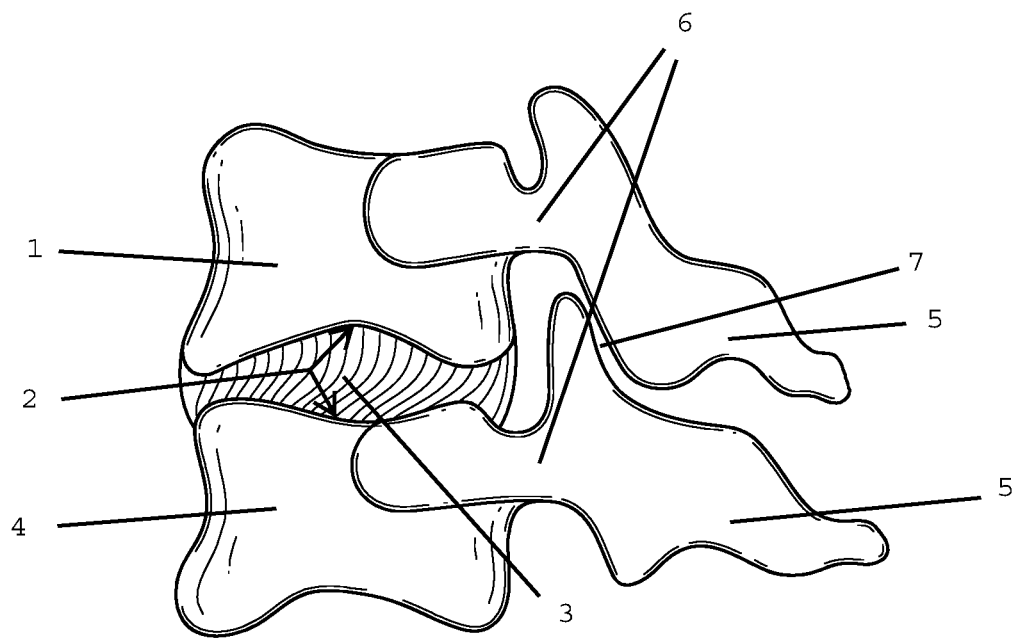
FIGS. 1A and 1B show a sagittal view of a functional spinal unit and an axial view of a vertebral body.
Figure 1B:
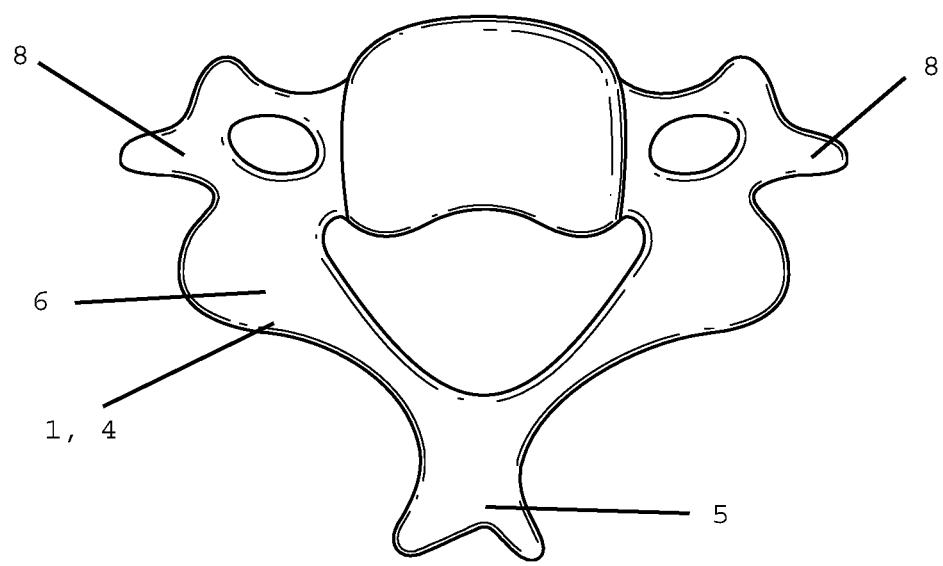

Implant devices and methods disclosed herein provide improved two part intervertebral/cervical disc prostheses for total cervical disc replacement which have two separate independent centers of rotation or "CORs" for flexion/extension and side-bending/rotation and the COR for flexion/extension is operable to be widely variable and further, the range of motion for side-bending and coupled rotation is hardly restricted by the flexion/extension angle after implantation.

As disclosed herein the two parts, partners, or members of one or more aspects of the invention may form a coupling, joint, or pair of articulating, sliding or bearing surfaces operable to replace a damaged intervertebral disc and/or posterior elements of a functional spinal unit.

One or more embodiments of the intervertebral disc implant described herein provides for dorsoventral motion (flexion/extension) and laterolateral motion (side-bending) and rotation independently from each other over independent centers of rotation with amplitudes that differ in magnitude and follow a cranially convex curve with a variable radius for dorsoventral motion (flexion/extension), but follow a caudally convex curve with a defined radius for laterolateral motion (side-bending).

The dorsoventral motion (flexion/extension) over the variable center of rotation, which results in a variable extent of dorsoventral translation together with dorsoventral rotation (flexion/extension), may be facilitated by the articulation of the cranial (superior) member with the convex projection within the saddle shaped projection of the caudal (inferior) member in a manner that allows dorsoventral rotation (flexion/extension) of the cranial (superior) member, and/or rolling and/or gliding over the convex articulation of the caudal (inferior) member.

The independent laterolateral motion (side-bending) may be facilitated by the articulation of the cranial (superior) member with the convex projection within the hyperbolic paraboloid "saddle-like" convex-concave articulation of the caudal (inferior) member in a manner that allows laterolateral rotation (side-bending) over a defined center of rotation located above the articulation of the two members independent from the momentary flexion/extension-angle or the momentary dorsoventral translation amplitude.

The independent transversal rotation (rotation) is facilitated by the articulation of the cranial (superior) member with the convex projection within the saddle shaped projection of the caudal (inferior) member in a manner that the cranial (superior) member may always rotate around a fictitious vertical axis independent from the momentary flexion/extension-angle or the momentary dorsoventral translation amplitude or the momentary side-bending-angle, and the cranial (superior) member also may always rotate around a fictitious axis that is perpendicular to the endplate of the cranial (superior) member independent from the momentary flexion/extension-angle or the momentary dorsoventral translation amplitude or the momentary side-bending-angle.

The different motion-angles, curves and amplitudes, together with the independent ability for coupled laterolateral motion (side-bending) and rotation of a cervical two part disc prosthesis, according to certain embodiments of the intervention, mimic the natural kinematics of a cervical intervertebral disc.

Figure 2:
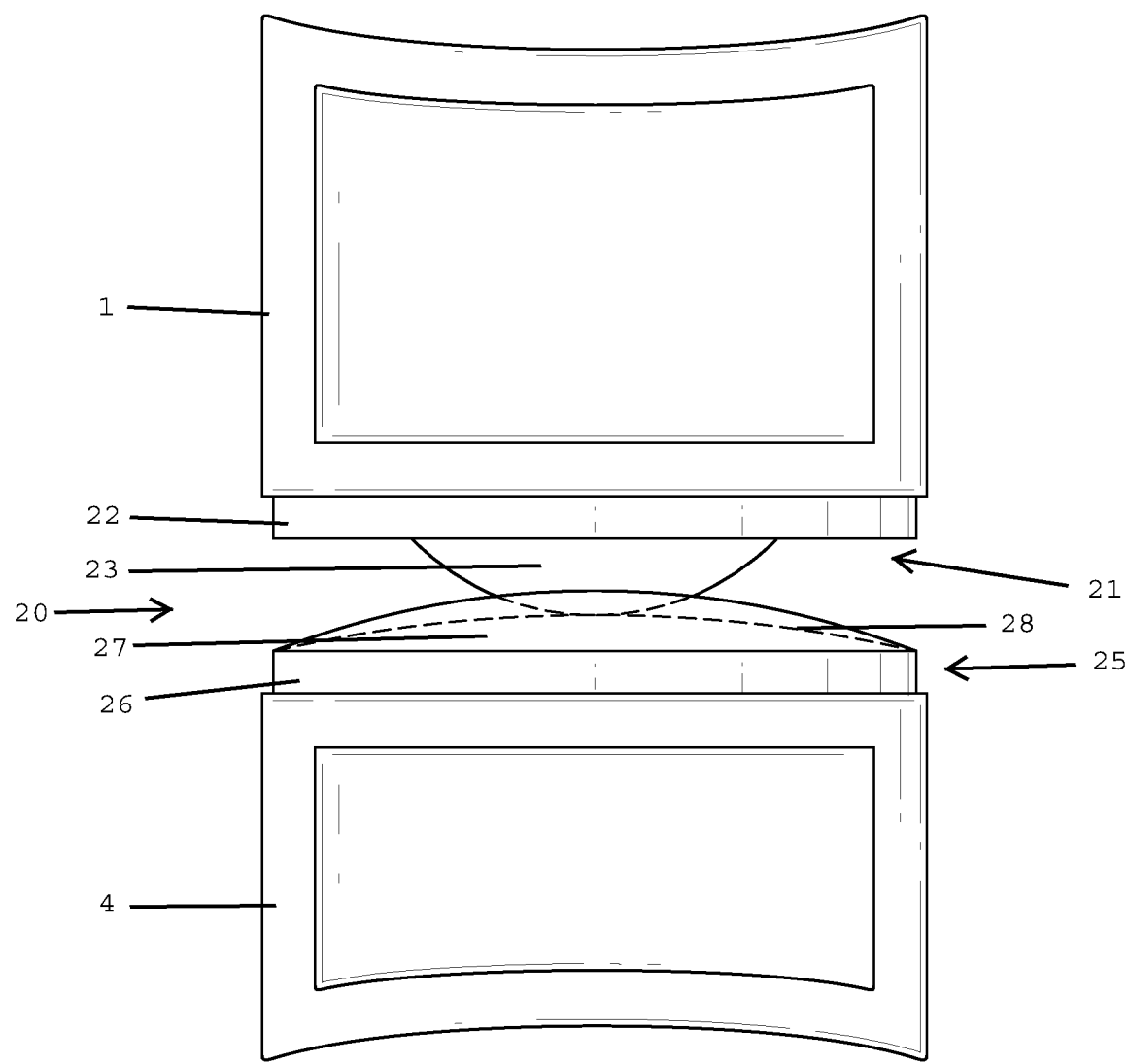
FIG. 2 shows a side-view of a concept of a intervertebral disc implant positioned between opposing vertebral bodies, the posterior elements are not shown.

Turning to the figures, FIG. 2 illustrates one embodiment of one or more aspects of the invention in its implanted position between two opposing vertebral bodies 1, 4. The intervertebral disc implant 20 is shown from a side-view or sagittal plane perspective as two paired articulating sliding members, where the upper or superior member 21 on its upper surface has a vertebral engagement portion or baseplate 22 and is adapted for a firm assembly to the upper vertebral body 1. Extending from the baseplate 22 is a convex projection 23 that has a preferably spherically convex curvature defining a bearing surface. The lower or inferior member 25 has on its lower surface a vertebral engagement portion or baseplate 26 and is adapted for a firm assembly to the lower vertebral body 4. The opposing upper surface of the baseplate 26 has a saddle shaped projection 27 which is convex in its longitudinal anterior-posterior extension along a first axis A1 with a diameter approximately double (though other ratios are possible) the diameter of the preferably spherically convex projection 23 of the superior member 21, and which is concave in its transversal lateral extent along a second axis A2 with approximately the same diameter (or within 1-5 mm) as the spherically convex projection 23 of the superior member 21. The superior member 21 is also shown mated with and partially concealed by the concavity (along the anterior posterior axis or first axis A1 in the frontal plane) contours of the inferior member 25 as depicted by the dotted line 28.

Either member may be implanted along either the superior or inferior endplate of the respective vertebral body and are thus interchangeable; references made herein with such terms as "upper," "lower," "superior," "inferior," "first," and "second" should be construed accordingly in all embodiments describe herein. Also, although both bearing surfaces have been described in terms of circles and spheres other convexities and concavities and other shapes that are less symmetrical, contain one or more flat surfaces or have varying radii of curvatures such as an elongated, shallow or pitched "D" or curvilinear "hour glass" concavities along one or both axes are contemplated. Although most of the paired bearing surfaces extensions of various embodiments of the intervertebral disc implant include separate and distinct baseplates for contacting the opposing vertebral endplates, one or both baseplates can be eliminated and the opposing nonbearing surface of the projections can contact directly contact the endplate and affixed to it or held in place via friction or other means.

In order to better understand how the various intervertebral disc implant described herein function, a series of figures will be presented depicting how each member of the paired bearing surfaces in several implanted embodiments articulate relative to the other members and how natural physiologic motion of the spinal segment is preserved. The following series will show flexion, extension, and lateral bending with and without translation. Also shown will be implantations wherein the device is seemingly "malpositioned" yet it will be apparent the relatively natural physiologic motion is preserved between the segments. Finally, due to the manner in which the bearing surfaces are shaped and mated the device does not limit or restrict rotation (when not implanted the surfaces may be rotated 360 degrees), the posterior elements and ligaments do however control the degree when the device is implanted. Medial-lateral translation is limited or even prevented (except for minute play between the surfaces) but anterior-posterior translation is on limited in its accurate or curvilinear path or trajectory (perpendicular) along the anterior posterior axis. In some embodiments the inferior member include a flanged, rim, protrusion or stop surface that prevents further translation in either of both portions of the saddle shaped projection. The stop surface can be located at any point along the bearing surface such as the extreme ends of the baseplate or that area corresponding the edge of the endplate. Other locations could be chosen to prevent the tendency of slipped discs (limit anterior translation) or to lessen forces on the facet joins (limit posterior translation).

Figure 3A:
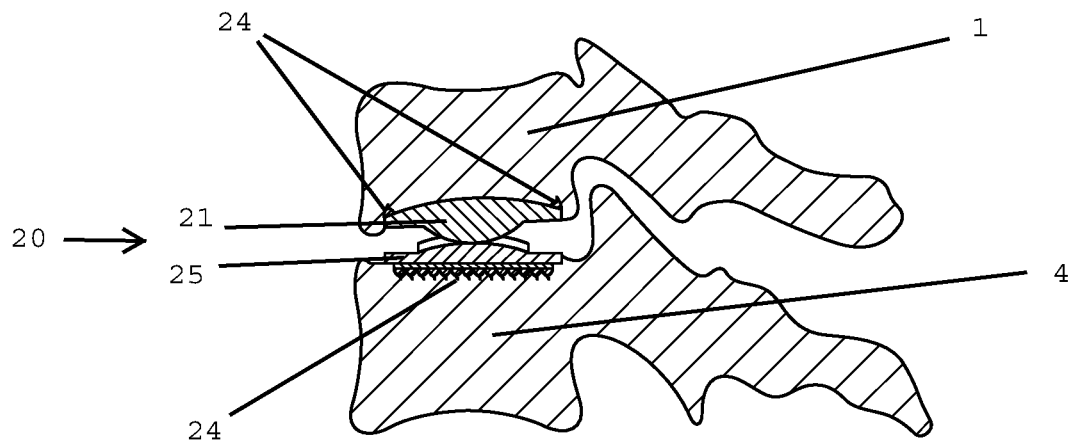
FIGS. 3A-3C show side-views of an intervertebral disc implant inserted between adjacent vertebral bodies undergoing flexion, extension, and translation following a short radius like in the C6/7-segment.
Figure 3B:
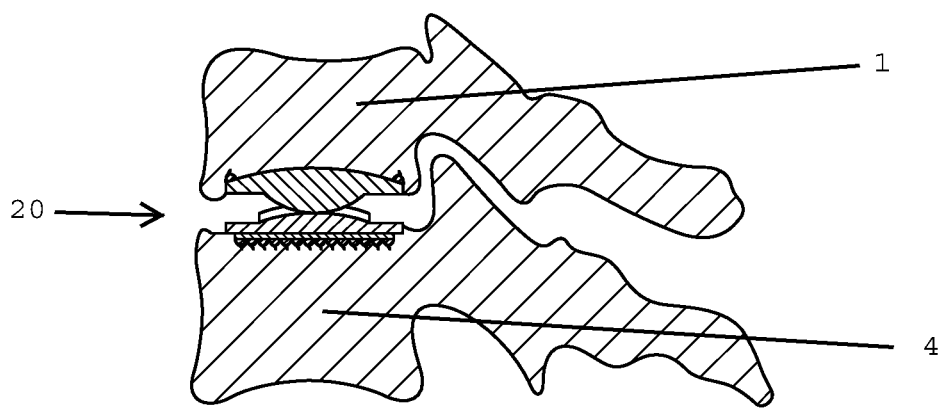
Figure 3C:
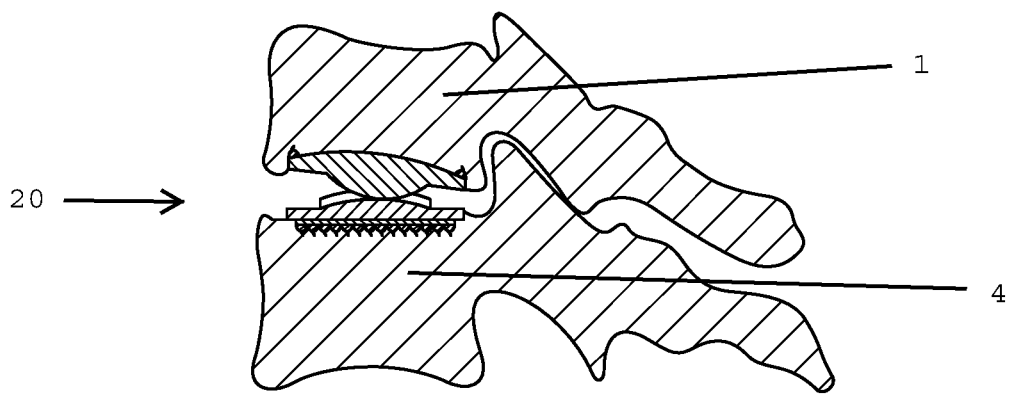

FIGS. 3A-3C depict a vertebral segment with an intervertebral disc implant 20 according to one aspect of the invention. In the sequence, shown from a sagittal, or side view, the convex projection 23 of the superior member 21 does not translate (or very minutely) along the anterior posterior axis of the saddle shaped projection 27 of the inferior member 25 which might be typical of the spinal motion found in cervical C6/7 vertebrae perhaps because of the smaller radius. FIGS. 3A-3C show the vertebral segment undergoing flexion, in a neutral position, and under extension respectively.

Figure 4A:
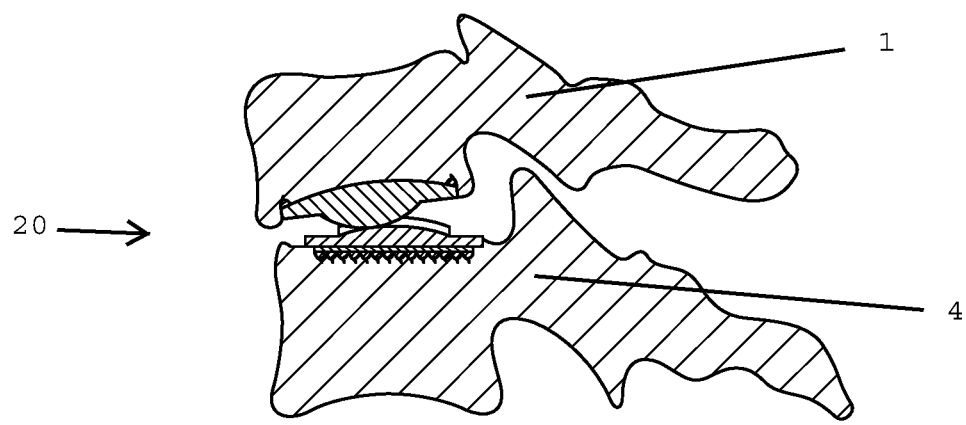
FIGS. 4A-4C show side-views of an intervertebral disc implant inserted between adjacent vertebral bodies undergoing flexion, extension, and translation following a wide radius like in the C3/4-segment.
Figure 4B:
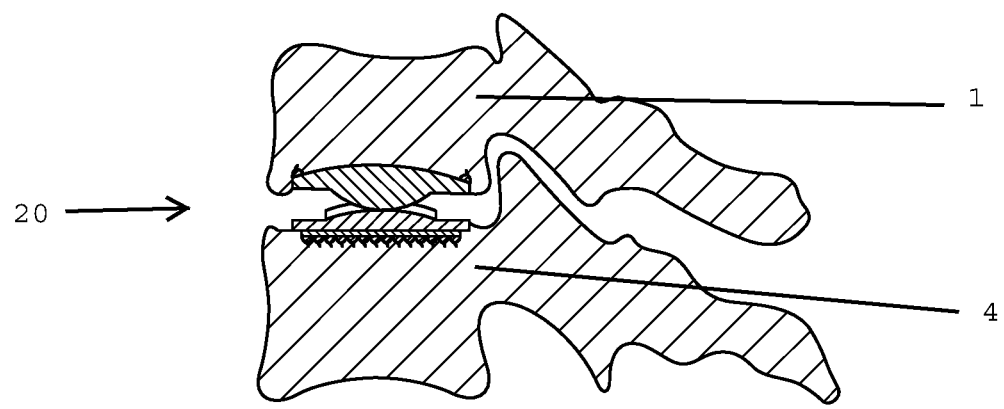
Figure 4C:
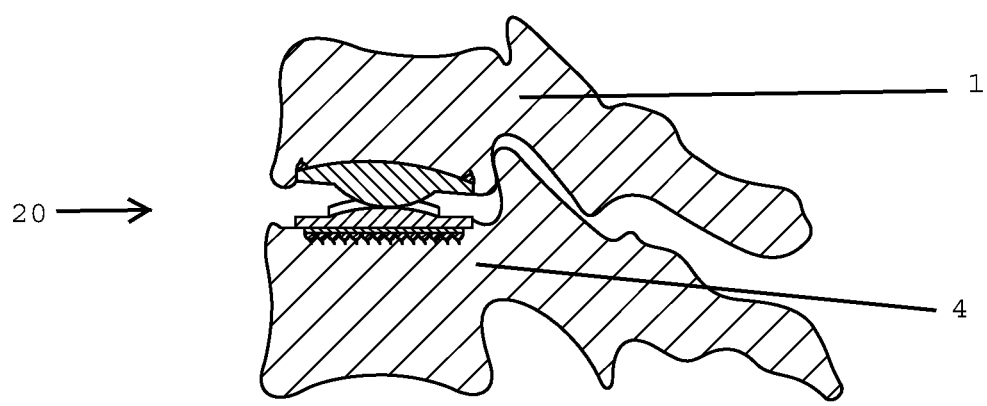
Figure 5A:
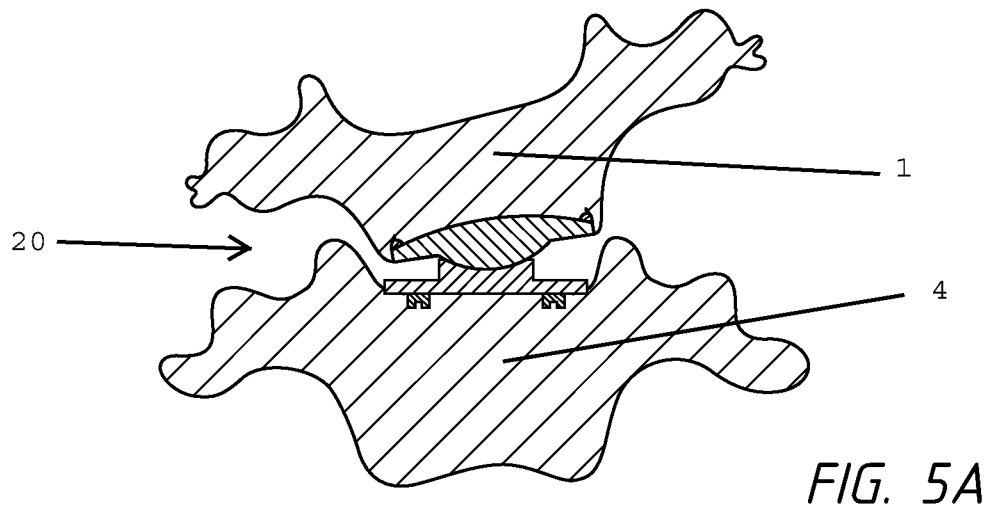
FIGS. 5A-5C show frontal views of an intervertebral disc implant inserted between adjacent vertebral bodies undergoing side-bending.
Figure 5B:
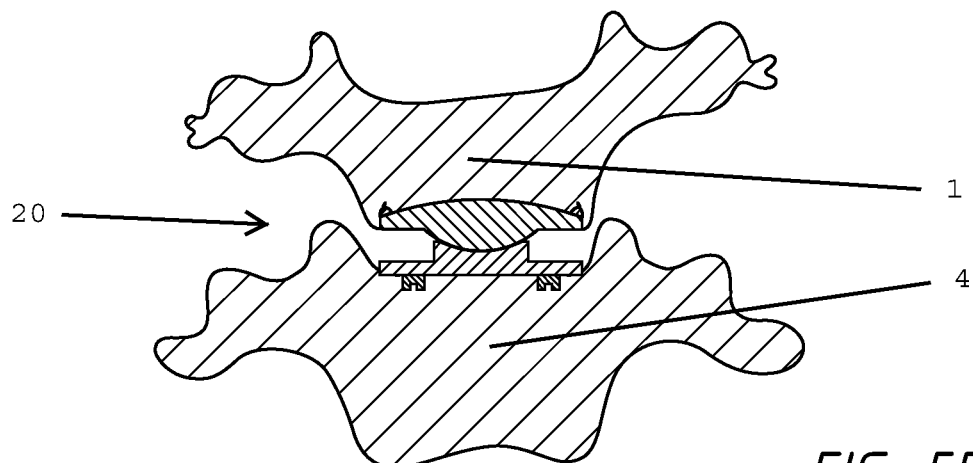
Figure 5C:
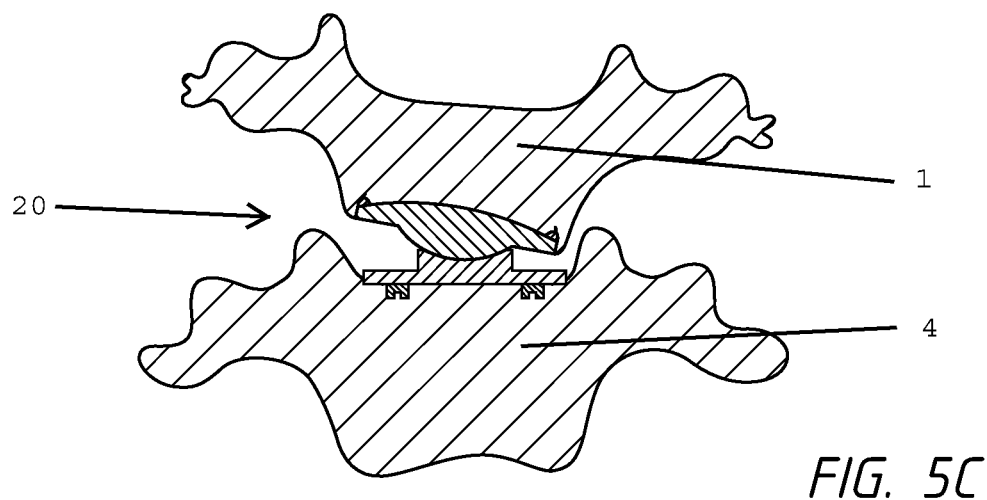

FIGS. 4A-4C depict a vertebral segment with an intervertebral disc implant 20 according to another aspect of the invention. In this sequence the convex projection 23 of the superior member 21 translates along the anterior posterior axis of the saddle shaped projection 27 of the inferior member 25 which might be typical of the spinal motion found in cervical C3/4 vertebrae perhaps because of the greater radius. FIGS. 4A-4C show the vertebral segment undergoing flexion, in a neutral position, and under extension respectively. As in the above sequence the COR for all positions shown is different because there has been rolling or sliding linear translation along the anterior posterior axis of the saddle shaped projection 27 of the inferior member 25 and the point of contact between the two bearing surfaces has changed. Also, in each position the bearing surfaces are free to rotate as in the above sequence. Finally, FIGS. 5A-5C show a intervertebral disc implant 20 from a frontal view implanted within a segment undergoing lateral bending. Here it can be seen that the COR for side-bending is independent of that of extension, neutral, and flexion.

Figure 6A:
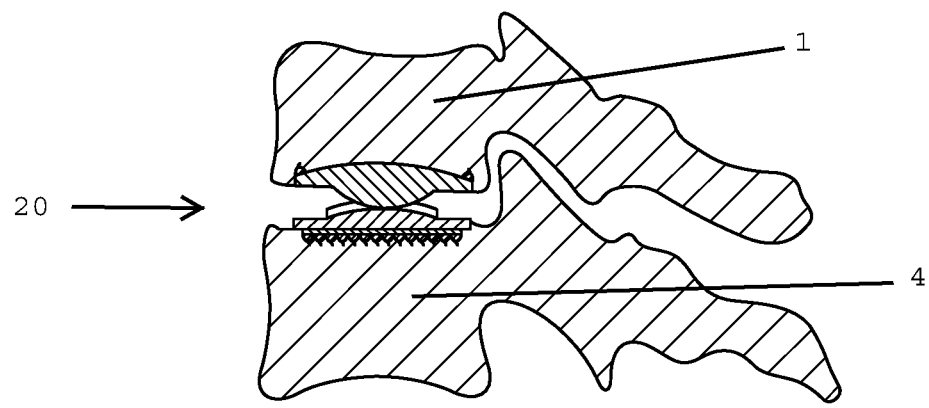
FIGS. 6A-6C show side-views of an intervertebral disc implant malpositioned between adjacent vertebral bodies undergoing flexion, extension, and translation following a short radius like in the C6/7-segment.
Figure 6B:
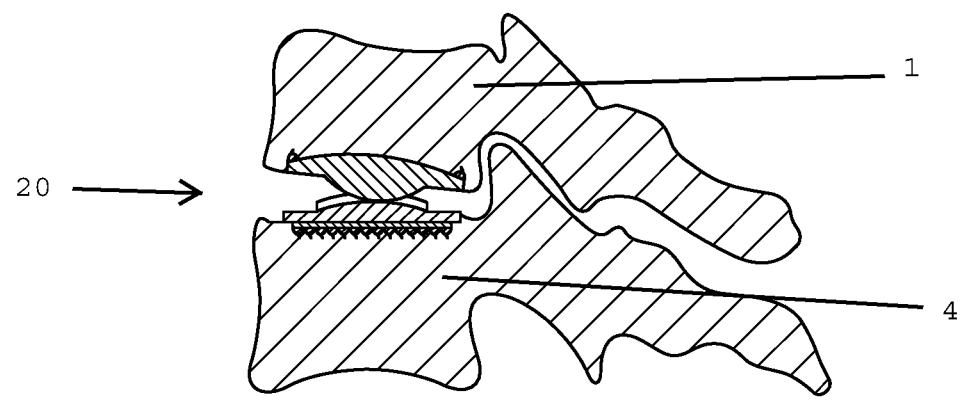
Figure 6C:
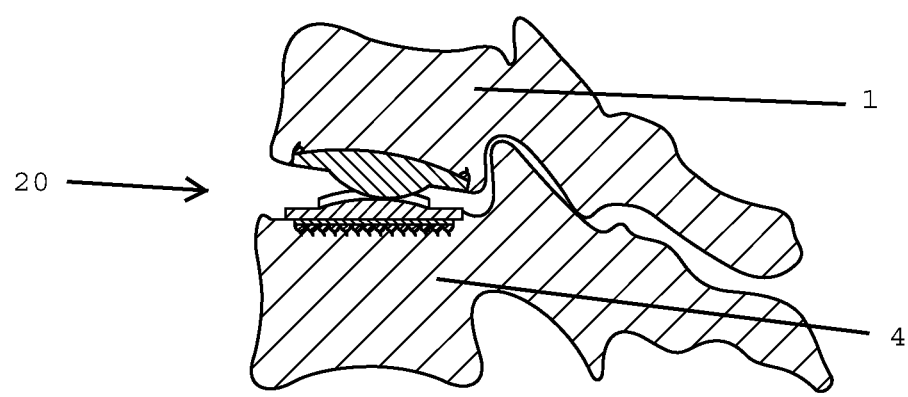
Figure 7A:
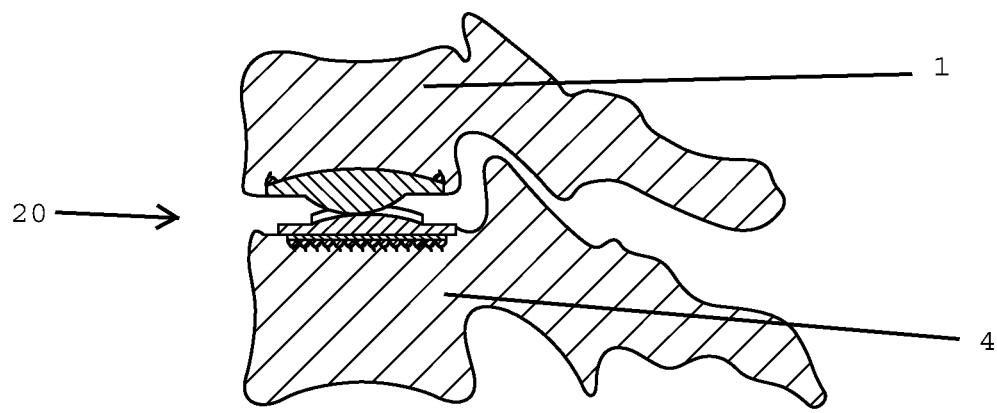
FIGS. 7A-7C show side-views of an intervertebral disc implant malpositioned between adjacent vertebral bodies undergoing flexion, extension, and translation following a wide radius like in the C3/4-segment.
Figure 7B:
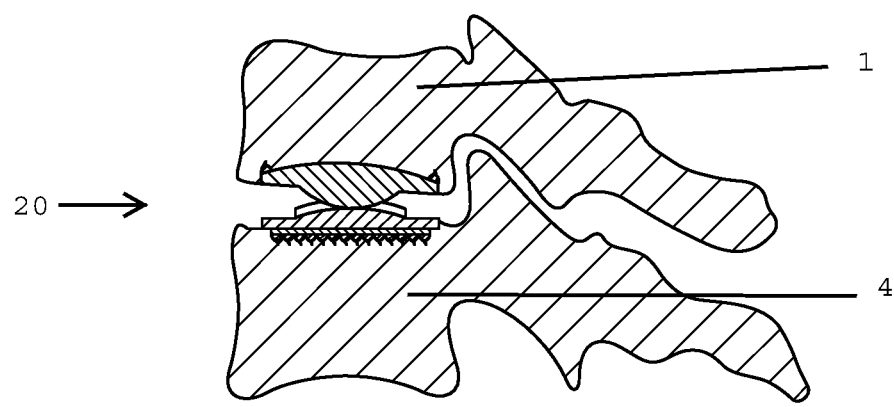
Figure 7C:
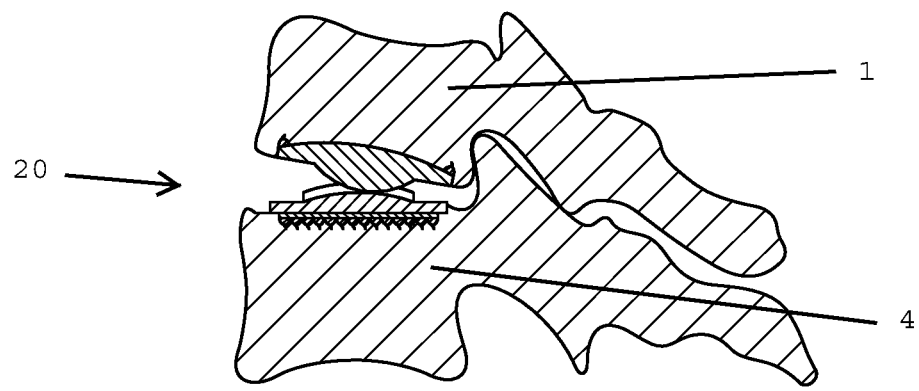
Figure 8A:
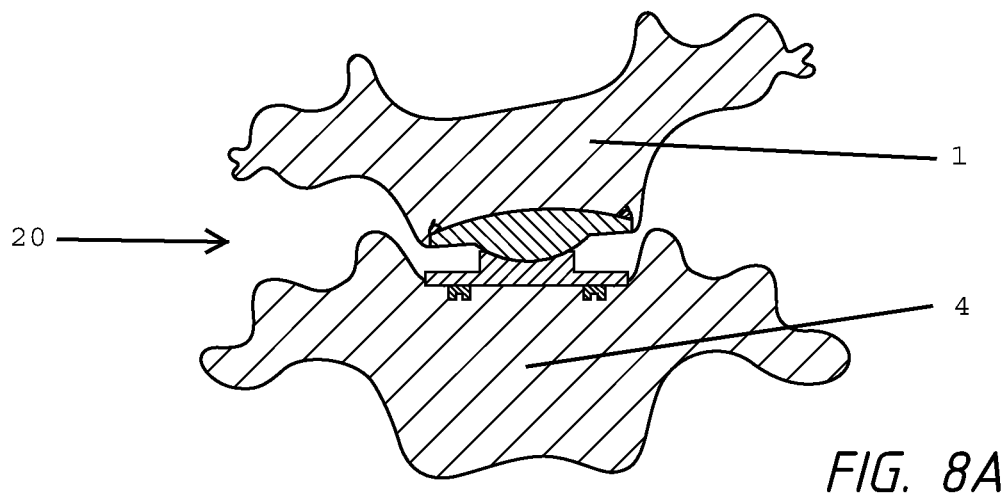
FIGS. 8A-8C show frontal views of an intervertebral disc implant malpositioned between adjacent vertebral bodies undergoing side-bending.
Figure 8B:
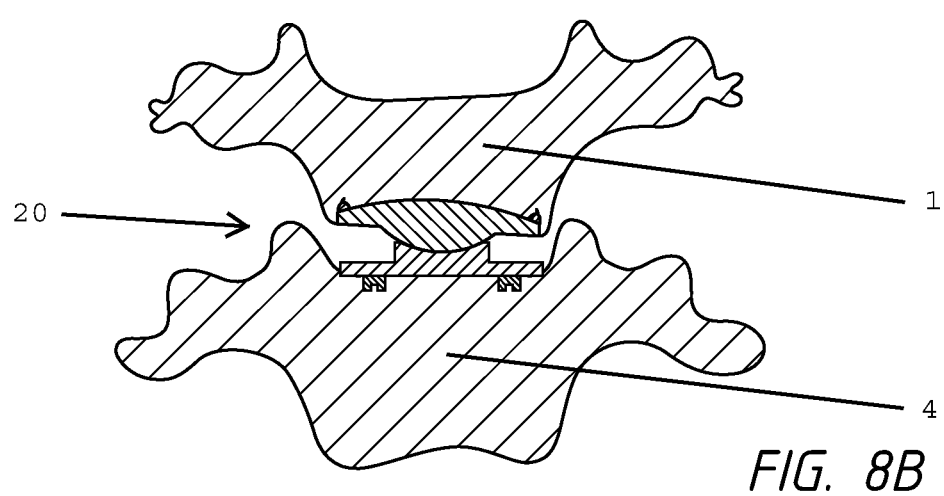
Figure 8C:
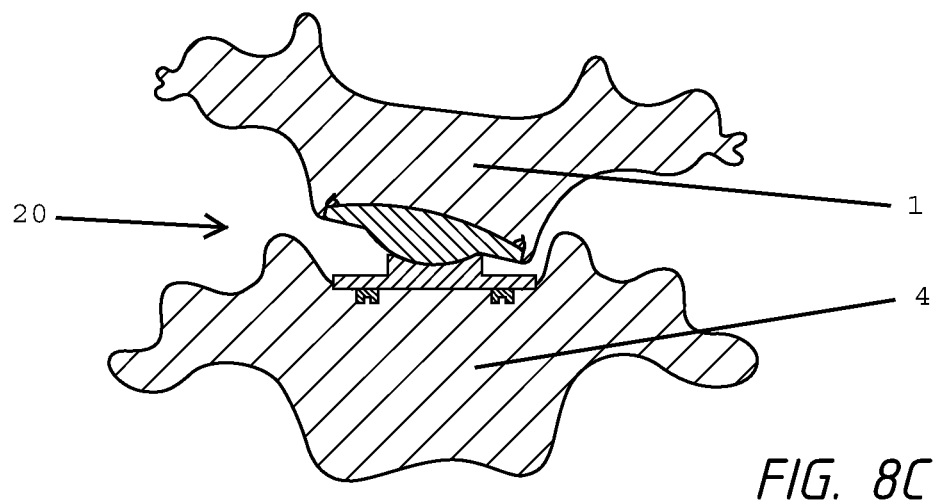

In the next sequence of figures, a similar device as depicted in FIGS. 3, 4 and 5 is implanted under less than ideal conditions as a consequence of the surgery itself or because of unfavorable or degenerated anatomy. Fortunately, the bearing surfaces of the paired implant will provide a spatial and kinematic relationship between the two vertebral bodies 1, 4 that permits load bearing and natural movement. Consequently, though seemingly "malpositioned" the intervertebral disc implant 20 still mimics the natural physiologic movement of the spinal segment. FIGS. 6A-6C show an intervertebral disc implant 20 implanted with a segment such the coupling of the bearing surfaces creates a lordotic condition perhaps because the superior member 21 was placed in too posteriorly. As depicted, this sequence does not involve translation along the saddle shaped projection 27 of the inferior member 25. As can be seen in FIG. 6B, the so-called neutral position appears to be in light extension and in FIG. 6C the vertebral segment appears to be hyper extended but still functional and load bearing. In FIGS. 7A-7C, the same intervertebral disc implant 20 is depicted undergoing translation in the same lordotically malpositioned implanted environment. The intervertebral disc implant 20 is shown in flexion, neutral, and extension respectively. Finally, FIGS. 8A-8C show the same intervertebral disc implant 20 from a frontal view implanted within a segment. The vertebral endplate 2 of the upper vertebral body 1 is malpositioned (not parallel and canted to the left). However, as can be seen in right bending, neutral, and left bending sequence, relative physiologic movement of the segment is preserved.

Figure 9:
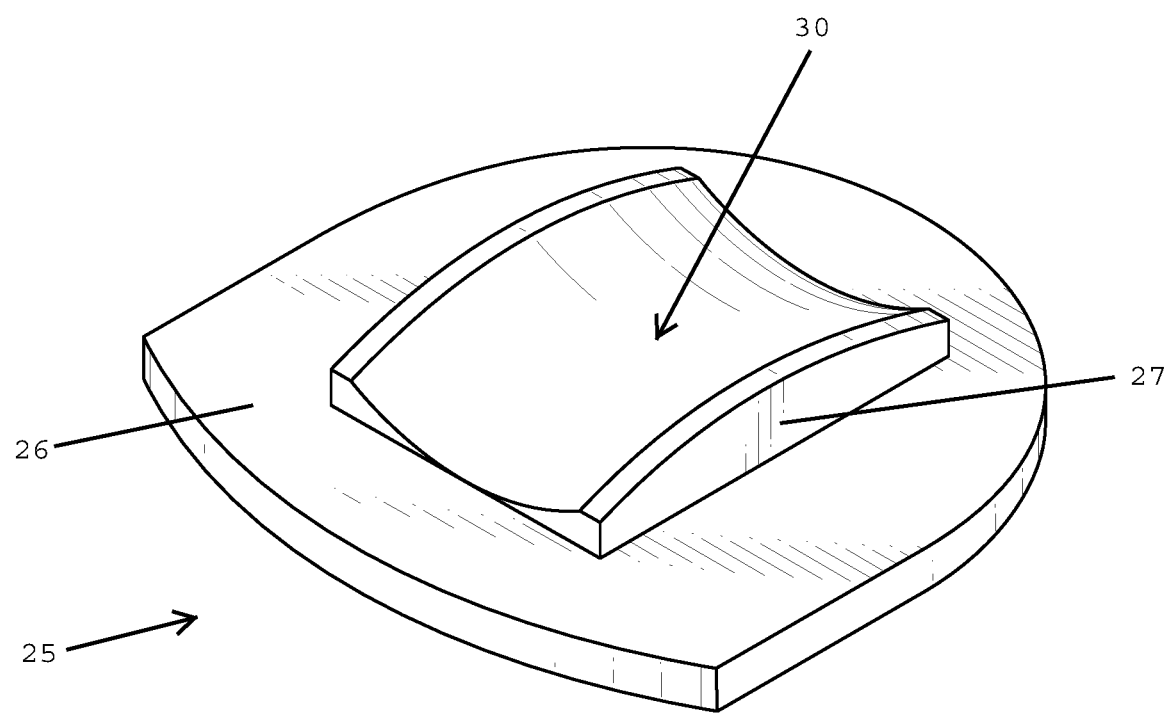
FIG. 9 shows a perspective view of a lower or inferior member of the intervertebral disc implant.
Figure 10:
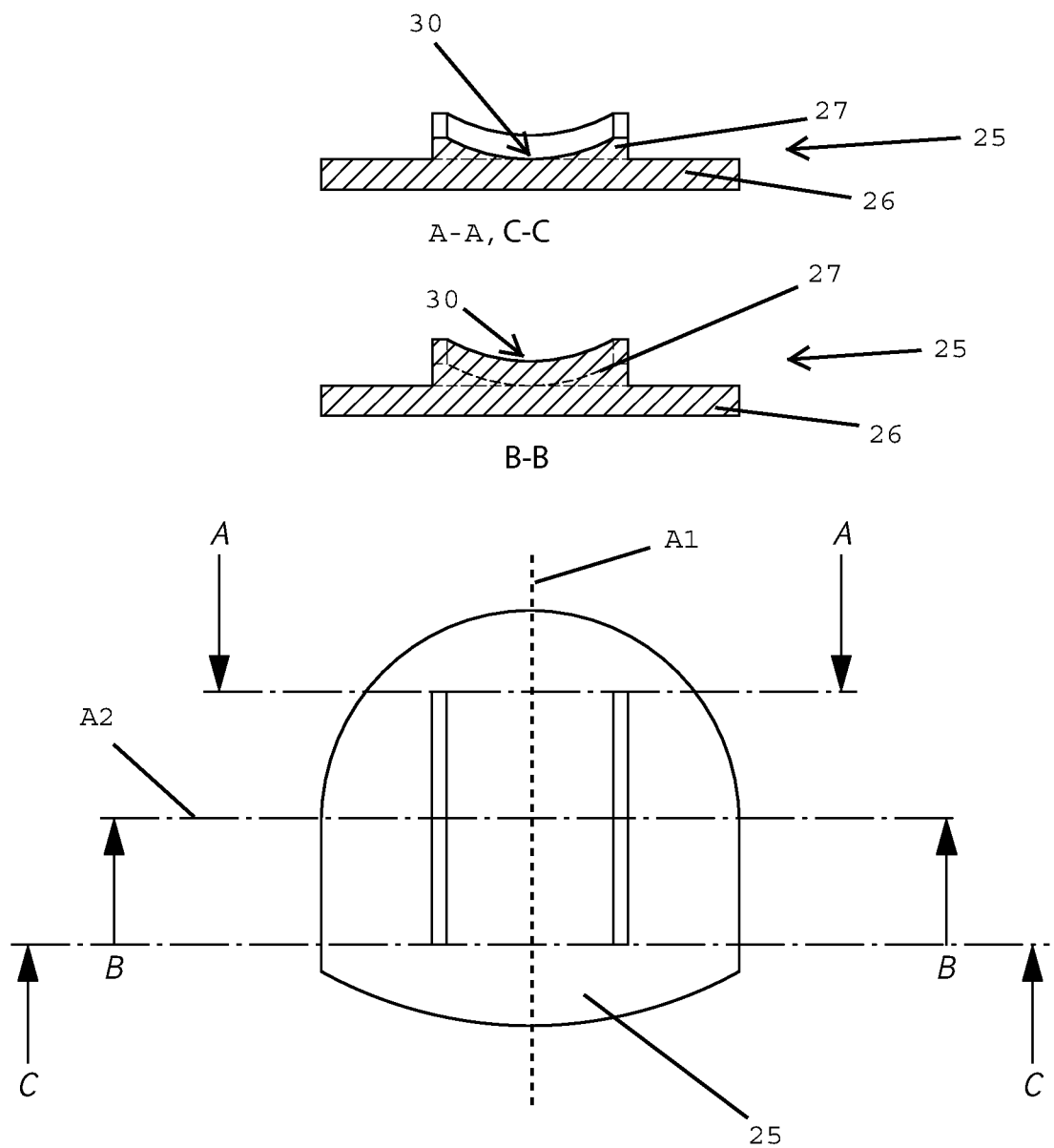
FIG. 10 shows a top view of the inferior member of the intervertebral disc implant according to FIG. 9 and cross-sectional views along the cutting lines A-A, B-B and C-C of FIG. 10.
Figure 11:
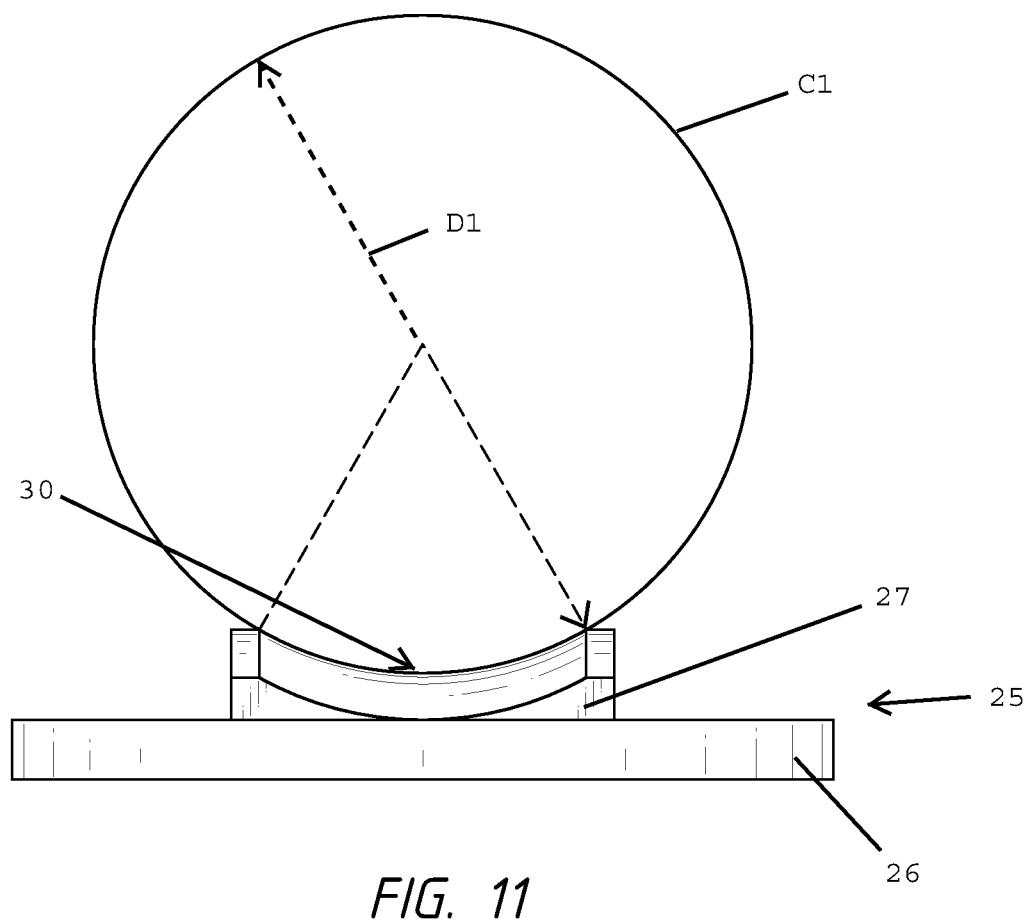
FIG. 11 shows a frontal view of the inferior member of the intervertebral disc implant in FIG. 9 and includes a reference circular cross-section of a torus including 60 degree section for determining the geometry of the concavity of the saddle shaped projection.
Figure 12A:
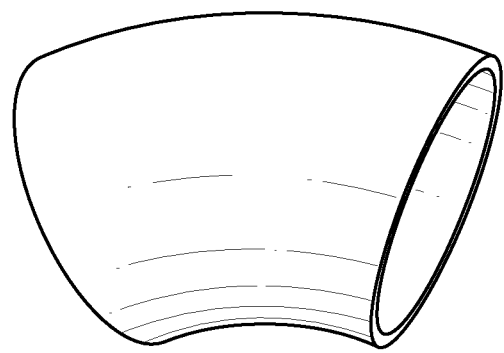
FIGS. 12A-12C shows a perspective view of the portion of a torus from which the shape of the "saddle-like" surface of the saddle shaped projection of the inferior member of the intervertebral disc implant can be derived.
Figure 12B:
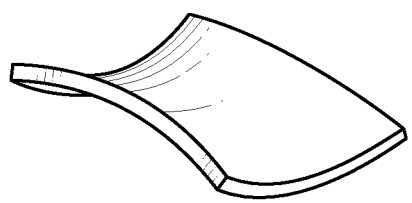
Figure 12C:
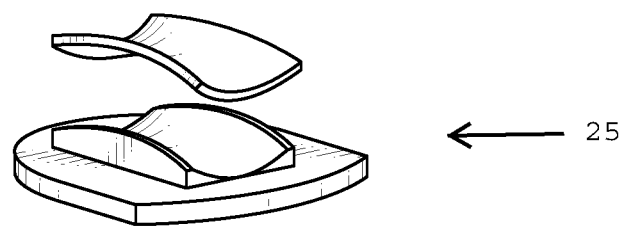

In one embodiment an intervertebral disc implant 20 according to one or more aspects of the invention is adapted especially for the use in the cervical spine includes a superior member 21 and an inferior member 25. Each member can include a baseplate 22, 26 with a projection 23, 27 on a first upper surface and a second lower opposing surface which is adapted for placement against an endplate 2 of the vertebral body 1, 4. Alternatively, the baseplate 22, 26 can simply be formed as the opposing side of the bearing surface of the projection 23, 27. Each projection 23, 27 or bearing surface of the paired members 21, 25 comprising the intervertebral disc implant 20 cooperates with the opposing bearing surface when both members 21, 25 are implanted between opposing vertebral bodies 1, 4. The saddle shaped projection 27 of the inferior member 25 is generally shaped to form a saddle-like structure that defines a convex-concave surface area. One such embodiment is depicted in FIGS. 9 and 10 and includes a baseplate 26 and saddle shaped projection 27 having a saddle-like surface 30. The surface 30 area is convex in the sagittal plane along axis A1 with a diameter D1 of approximately 12 mm (plus or minus 5 mm according to the different sizes of the implant) and represents a 45-degrees (or between 20 and 60 degrees) sector of a circle C1 in the sagittal plane with its "center" below. The surface 30 area is concave in the frontal section along axis A2 with a diameter D2 of approximately 6 mm (plus or minus 5 mm according to the different sizes of the implant) and represents a 60-degrees (or between 40 and 80 degrees) sector of a circle in the frontal plane with its "center" above. The surface 30 area both results from a 60-degrees rotation of the 45-degrees-convex-sagittal-plane-circle-sector in the frontal plane with a radius of approximately 6 mm (plus or minus 5 mm according to the different sizes of the implant) and its rotation—center approx. 6 mm (plus or minus 5 mm according to the different sizes of the implant) above the mid-sagittal section. The surface 30 can be further characterized as providing a 45-degrees rotation of the 60-degrees-concave-frontal-plane-circle sector in the sagittal plane with a radius of approximately 12 mm (plus or minus 5 mm according to the different sizes of the implant) and its rotation-center approximately 12 mm (plus or minus 5 mm according to the different sizes of the implant) below the mid-frontal section thus creating a saddle-like surface 30 with a sagittal plane convexity being lowest in the mid-sagittal plane, and a frontal-plane concavity being highest in the mid-frontal plane and is enclosed by a margin defined by a transversal semayt-plane cutting off the 45-degrees-convex-sagittal-plane-circle-sector. FIGS. 11 and 12A-12C show some of the geometric reference shapes for defining the concave and convex surface of the saddle shaped projection 27 of the inferior member 25 including a circle, torus, and saddle.

Figure 13A:
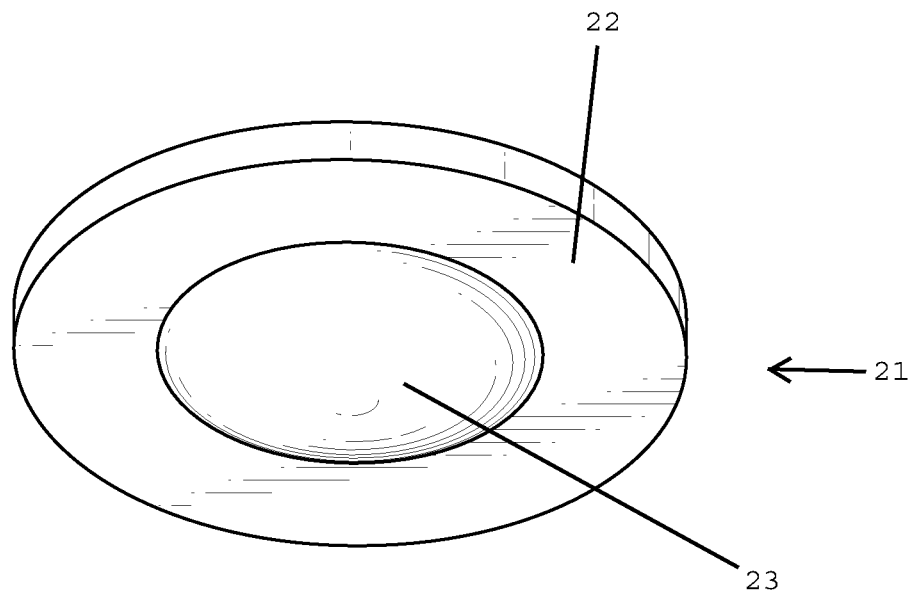
FIG. 13A shows a perspective view of an superior member of the intervertebral disc member.
Figure 13B:
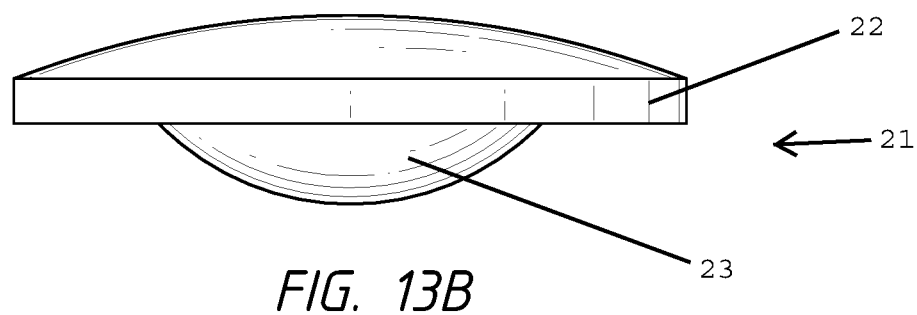
FIG. 13B shows a frontal view of the superior member in FIG. 13A.
Figure 13C:
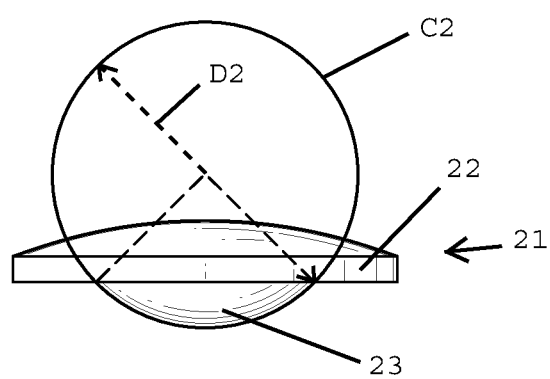
FIG. 13C shows a cross-sectional view of the superior member in FIG. 13A and includes a reference cross-section of a sphere for determining the geometry of the convex projection.

The convex projection 23 of the superior member 21 is generally shaped to form a convex, preferably spherical, surface area. One such embodiment is depicted in FIGS. 13A and 13B and includes a baseplate 22 and convex projection 23 having a convex-like surface. The surface area is convex both in the sagittal and in the frontal plane with a diameter D2 of approximately 6 mm (plus or minus 5 mm according to the different sizes of the implant) and represents a 90-degrees-sector of a sphere though other sectors between 70 and 110 are possible. The surface is generally congruent to the surface area of the inferior member 25 and its shape can be characterized as that which is enclosed by a margin defined by a transversal semayt-plane cutting off the 90-degrees ball-sector. This reference ball C2 is depicted in FIG. 13C.

In the implant orientation in which the superior member 21 and inferior member 25 are coupled such that the opposing extensions are mated or otherwise contacting each other several advantages will be apparent. The flat design of the margins or periphery of the opposing baseplates 22, 26 and the height of the convex projection 23 of the superior member 21 allow unrestricted motion within the physiological range of motion of cervical motion segments for flexion/extension, side-bending and rotation without contact of the edges. Further, the saddle shaped projection 27 of the inferior member 25 together with the convex projection 23 of the superior member 21 allow anterior-posterior sliding of the superior member 21 over the inferior member 25 upon the convexity of the inferior member 25. The design further facilitates anterior-posterior rotation of the superior member 21 upon the inferior member 25 and anterior-posterior rolling of the superior member 21 upon the inferior member 25. Also, facilitated is side-bending (lateral rotation) of the superior member 21 upon the inferior member 25 with the center of rotation above. Also, the design further permits transversal rotation of the superior member 21 upon the inferior member 25 therefore coupled motion for side-bending (lateral rotation) and transversal rotation over a physiological oblique sagittal rotation-axis independent from the momentary extent of flexion/extension and therefore flexion/extension with a widely variable physiological center of rotation independent from the momentary extent of side-bending and/or rotation.

Regarding the material of the intervertebral disc implant 20, as per the intervention, the members 21, 25 are preferably manufactured from well-established materials from implantation techniques like titanium, titanium alloys, cobalt-chrome-alloys, tantalum alloys, carbon-fiber-composites, PEEK, ceramics, polyethylene, or a combination of any of the above, for instance. The articulating surfaces are preferably high gloss polished in order to minimize abrasion following the low-friction principle. It is further intended to cover the outer part of the two endplates 2 with porous titanium or similar materials or bio-active materials, for instance, in order to promote bone ingrowth at the bone-prosthesis-interface.

In a further preferred design, as per the intervention, it is also intended to include polyethylene or other suitable plastics as a shock-absorbent layer in at least a portion of one of the members 21, 25 along the baseplate 22, 26 or projection 23, 27.

In a favored design, as per the intervention, the edge of the inferior member 25 has a trapezoid design close to the natural anatomy of the superior endplate of a cervical vertebral body with the longer side of the trapezoid being anteriorly and slightly curved, and the short side of the trapezoid posteriorly and straight. In this design, the outer side of this trapezoid endplate, which is facing the superior endplate of the vertebral body caudal to the respective disc space, has means for a firm fixation inside the vertebral body's endplate, like 1 or 2 keels, for instance, or spikes or a combination of any suitable devices for fixation of a disc prosthesis at a vertebral body's endplate.

Figure 14:
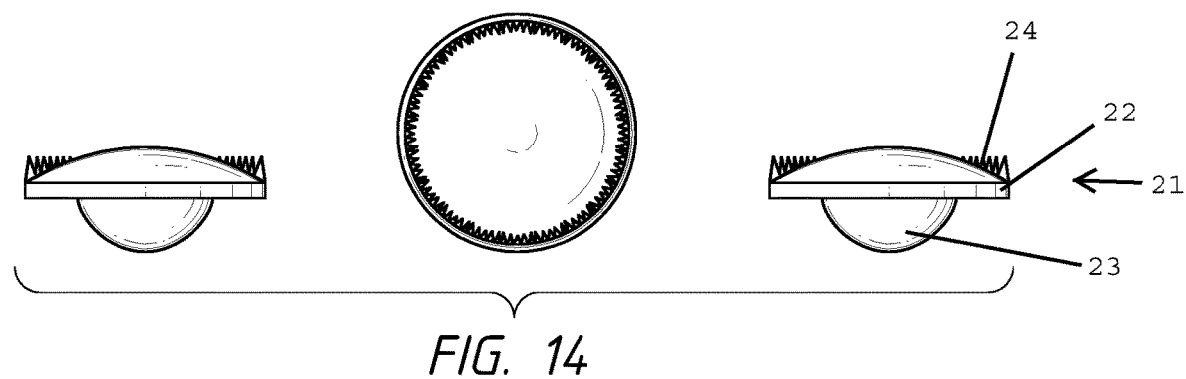
FIG. 14-17 shows various fixation modalities of the superior member and the inferior member of the intervertebral disc implant in frontal, side, top and bottom views.
Figure 15:
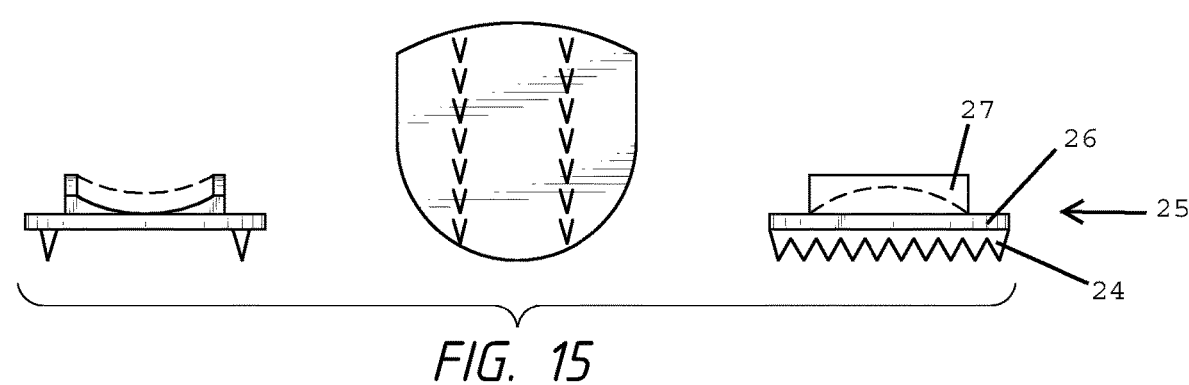
Figure 16:
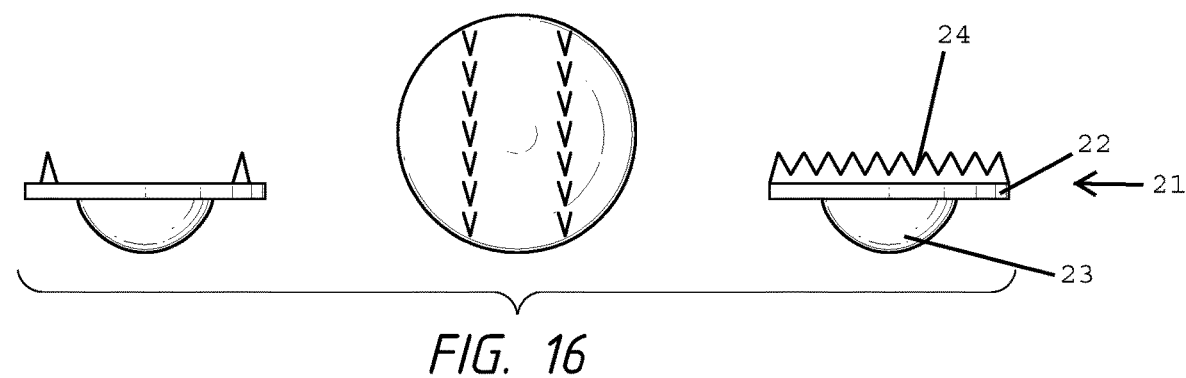
Figure 17:
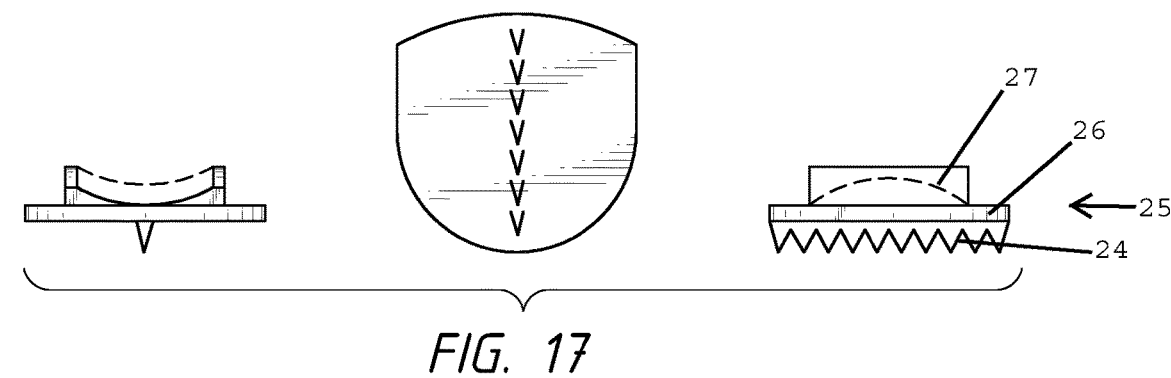

In a favored design, as per one aspect of the intervention, the edge of the superior member 21 has a slightly curved spherical dome-like design close to the natural anatomy of the inferior endplate of a cervical vertebral body. In this design, the outer side of this dome-shaped endplate, which is facing the inferior endplate of the vertebral body cranial to the respective disc space, has means for a firm fixation inside the vertebral body's endplate, like one or more anchors 24 or keels as shown in FIG. 14 which may be blade like or formed from a row of spikes, a full or portion of a circular rim or flange as shown in FIG. 15, or various patterns of spikes or a combination of any suitable devices, such as adhesives, for fixation of an intervertebral disc implant 20 at an endplate 2 of a vertebral body 1, 4.

In a further design, both endplates have a trapezoid design as described above, both with suitable devices or anchors 24 for fixation at the adjacent endplate 2 of the vertebral body 1, 4.

In a further design, both endplates have a slightly curved spherical dome-shaped design as described above, both with suitable devices for fixation at the adjacent vertebral bodies' endplates.

In a favored design, the outer part of the edge of the endplate of the superior member 21, which faces the inferior endplate 2 of the vertebral body 1 cranial to the respective disc space, is—irrespective of its shape, whether it is trapezoid or dome-shaped or other—slightly angled with respect to the inner surface of the edge of this sliding member in a manner that a lordotic angle of the outer surfaces of the endplates against each other of approximately 7 degrees (or between 5 and 15 degrees) is created when the inner surfaces of the edges of the two sliding members are parallel and the implant is in neutral position.

In a further design, the outer part of the edge of the endplate of the superior member 21, which faces the inferior endplate 2 of the vertebral body 1 cranial to the respective disc space, is—irrespective of its shape, whether it is trapezoid or dome-shaped or other—not angled, therefore the outer surfaces of the endplates are parallel against each other when the inner surfaces of the edges of the two sliding members are parallel and the implant is in neutral position.

Certain preferred embodiments adapted especially for a cervical intervertebral disc implant may include the following dimensional considerations for a plate member or articulating member, a maximal width (lateral extension in a frontal section) of 13 to 21 mm, including about 13 mm, about 15 mm, about 17 mm, about 19 mm, or about 21 mm, a maximal depth (dorsoventral extension in a sagittal section) of 12 to 18 mm, including about 12 mm, about 14 mm, about 16 mm or about 18 mm, and a maximal height of 5 to 13 mm, including about 5 mm, about 7 mm, about 9 mm, about 11 mm, or about 13 mm.

In one method of delivery, the site between the selected vertebral bodies is prepared and at least a portion of the intervertebral disc implant is removed. The vertebral bodies may be distracted with instruments or by positioning the patient's neck or spine section along a convex surface. If the angle of the surgical approach is not directly anterior or posterior but rather anterior lateral or posterior lateral or lateral then the inferior member with the convex/concave projection can be delivered with the concave portion oriented perpendicularly to the axis of the implantation trajectory (or surgical approach). After it is mated with the superior member with the convex projection it can then be rotated such that the concave surface of the superior member is oriented centrally along the endplate and perpendicular to the longitudinal anterior posterior axis and the convex portion is perpendicular to the transverse lateral axis. Thus either member may be inserted first but the inferior member having the convex/concave projection or extension must be inserted along a precise trajectory to allow proper mating of the bearing surfaces before the inferior surface can be rotated into proper position along the anterior posterior axis. Thereafter, each baseplate can be secured to the corresponding vertebral endplate. As such, translation is facilitated along the posterior lateral axis but restricted or limited along transverse lateral axis but as describe above rotation, flexion, extension and lateral bending characteristics are preserved.

While various embodiments of the invention have been described with reference to preferred and exemplary embodiments, it will be understood by those skilled in the art that a variety of modifications, additions and deletions are within the scope of the invention, as defined by the following claims.

The invention claimed is:

1. An intervertebral disc implant for implanting between two opposing vertebral bodies comprising:
    a superior member with opposing first and second surfaces, the superior member first surface is adapted for attachment to a vertebral endplate of one vertebral body, and the superior member second surface comprises a spherically convex projection extending from the second surface; and
    an inferior member with opposing first and second surfaces, the inferior member first surface is adapted for attachment to a vertebral endplate of the opposing vertebral body, wherein
    the inferior member second surface comprises a saddle shaped projection having a convex profile along a first axis sagittal plane and a concave profile along a second axis in a transverse plane; wherein
    the spherically convex projection of the superior member and the saddle shaped projection of the inferior member are adapted to congruently fit together and facilitate rotation, pivoting and translation along the sagittal plane of the two opposing vertebral bodies when implanted there between; wherein
    the spherically convex projection of the superior member is convex in three dimensions; and wherein
    a first center of rotation for flexion-extension is located below where the superior member and the inferior member fit together, and a second center of rotation for lateral bending is located above where the superior member and the inferior member fit together.

2. The intervertebral disc implant according to claim 1, wherein the spherically convex projection extending from the second surface of the superior member is defined by a 70-110 degree secant plane of a sphere having a diameter between 2 and 10 mm.

3. The intervertebral disc implant according to claim 1, wherein the saddle shaped projection extending from the second surface of the inferior member comprises a sector of a first circle (C1) between 40-50 degrees and with a diameter (D1) of the first circle (C1) between 6 and 18 mm in length, and wherein the saddle shaped projection in the transverse plane comprises a concave surface defined by sector of a second circle (C2) between 55-65 degrees and with a diameter (D2) of the second circle (C2) between 4 and 10 mm.

4. The intervertebral disc implant according to claim 1, wherein the superior member has a base plate with opposing superior member base plate first and second surfaces, the superior member base plate first surface is adapted for attachment to a vertebral endplate of one vertebral body, and the superior member base plate second surface comprises the spherically convex projection extending from the superior member second surface; and the inferior member having a base plate with opposing inferior member base plate first and second surfaces, the inferior member base plate first surface is adapted for attachment to a vertebral endplate of the opposing vertebral body and the inferior member base plate second surface comprises the saddle shaped projection extending from the inferior member second surface.

5. The intervertebral disc implant according to claim 1, wherein the spherically convex projection of the superior member rides along the concave portion of the saddle shaped projection of the inferior member in an arcuate path along the first axis thereby allowing multiple centers of rotation between the superior member and the inferior member including the first center of rotation and the second center of rotation.

6. The intervertebral disc implant according to claim 1 wherein the second axis (A2) of the concave profile of the saddle shaped projection is perpendicular to the first axis (A1) of the convex profile of the saddle shaped projection of the inferior member, thereby allowing multiple centers of rotation between the superior member and the inferior member including the first center of rotation and the second center of rotation and allowing travel along the first axis (A1).

7. The intervertebral disc implant according to claim 1, wherein the superior member and the inferior member further comprises an anchor for anchoring to a vertebral endplate to the vertebral bodies.

8. The intervertebral disc implant according to claim 1, wherein the translation between the spherically convex projection of the superior member and the saddle shaped projection of the inferior member along the first axis (A1) is curvilinear.

9. The intervertebral disc implant according to claim 1 wherein the translation between the spherically convex projection of the superior member and the saddle shaped projection of the inferior member along the second axis (A2) is limited.

10. The intervertebral disc implant according to claim 1 wherein the translation between the spherically convex projection of the superior member and the saddle shaped projection of the inferior member along the second axis (A2) is prevented.

11. An intervertebral disc implant for implanting between two opposing vertebral bodies comprising:

a superior member with opposing first and second surfaces, the superior member first surface is adapted for attachment to a vertebral endplate of one vertebral body, and the superior member second surface comprises a spherically convex projection extending from the second surface; and an inferior member with opposing first and second surfaces, the inferior member first surface is adapted for attachment to a vertebral endplate of the opposing vertebral body, wherein the inferior member second surface comprises a saddle shaped projection having a convex profile along a first axis sagittal plane and a concave profile along a second axis in a transverse plane; wherein the spherically convex projection of the superior member and the saddle shaped projection of the inferior member are adapted to congruently fit together and facilitate rotation, pivoting and translation along the sagittal plane of the two opposing vertebral bodies when implanted there between, wherein the rotation between the spherically convex projection of the superior member and the saddle shaped projection of the inferior member is unlimited; and wherein a first center of rotation for flexion-extension is located below where the superior member and the inferior member fit together, and a second center of rotation for lateral bending is located above where the superior member and the inferior member fit together.

* * * * *